(12) United States Patent
Fillatti et al.

(10) Patent No.: US 10,358,649 B2
(45) Date of Patent: *Jul. 23, 2019

(54) IN VIVO ASSEMBLY OF TRANSCRIPTION UNITS

(71) Applicant: MONSANTO TECHNOLOGY LLC, St. Louis, MO (US)

(72) Inventors: JoAnne Fillatti, Davis, CA (US); Larry Gilbertson, Chesterfield, MO (US); Toni Voelker, Davis, CA (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/466,669

(22) Filed: Mar. 22, 2017

(65) Prior Publication Data

US 2017/0191074 A1   Jul. 6, 2017

Related U.S. Application Data

(63) Continuation of application No. 14/109,835, filed on Dec. 17, 2013, now Pat. No. 9,611,484, which is a continuation of application No. 11/057,071, filed on Feb. 11, 2005, now Pat. No. 8,609,934.

(60) Provisional application No. 60/544,690, filed on Feb. 13, 2004.

(51) Int. Cl.
   *C12N 15/82*   (2006.01)
   *C12N 15/63*   (2006.01)

(52) U.S. Cl.
   CPC ......... *C12N 15/8201* (2013.01); *C12N 15/63* (2013.01); *C12N 15/8203* (2013.01); *C12N 15/8213* (2013.01); *C12N 15/8216* (2013.01); *C12N 15/8218* (2013.01); *C12N 15/8247* (2013.01)

(58) Field of Classification Search
   None
   See application file for complete search history.

(56) References Cited

U.S. PATENT DOCUMENTS

| | | | | |
|---|---|---|---|---|
| 5,545,818 A | * | 8/1996 | McBride | C07K 14/325 800/279 |
| 6,326,193 B1 | * | 12/2001 | Liu | A01N 63/00 435/235.1 |
| 6,506,559 B1 | | 1/2003 | Fire et al. | |
| 8,609,934 B2 | * | 12/2013 | Fillatti | C12N 15/63 435/320.1 |
| 9,611,484 B2 | * | 4/2017 | Fillatti | C12N 15/63 |
| 2003/0150017 A1 | * | 8/2003 | Mesa | C07K 14/4354 800/279 |
| 2004/0002077 A1 | | 1/2004 | Taira et al. | |
| 2006/0117400 A1 | * | 6/2006 | Herz | C12N 15/8214 800/278 |
| 2007/0124831 A1 | | 5/2007 | Giritch et al. | |

OTHER PUBLICATIONS

Wicke et al (2011, Plant. Mol. Biol. 76:272-297).*
Communication pursuant to Article 94(3) EPC dated May 26, 2010 received in corresponding application 05713532.9-2403.
Communication from EPO pursuant to Article 94(3) EPC dated Jun. 4, 2009 received in corresponding application 05713532.9-2401.
Communication from EPO pursuant to Article 94(3) EPC dated Oct. 7, 2008 received in corresponding application 05713532.9-2401.
Communication from the EPO, Supplementary Search Report, dated Jun. 29, 2007 received in corresponding application 05713532.9-2401.
Chuang et al., "Specific and heritable genetic inteference by double-stranded RNA in *Arabidopsis thaliana*," *PNAS* vol. 97(9); pp. 4985-4990; Apr. 25, 2000.
De Neve et al., "T-DNA Integration Patterns in Co-Transformed Plant Cells Suggest that T-DNA Repeats Originate from Co-Integration of Separate T-DNAs," *The Plant Journal* vol. 11(1); pp. 15-29; 1997.
De Buck et al., "The DNA Sequences of T-DNA Junctions Suggest that Complex T-DNA Loci are Formed by a Recombination Process Resembling T-DNA Integration," *The Plant Journal* vol. 20(3); pp. 295-304; 1999.
Fitzgerald et al., "Simultaneous silencing of multiples genes in the apple scab fungus, *Ventura inaequalis*, byexpression of RNA with chimeric inverted repeats," *Fungal Genetics and Biology* vol. 41; pp. 963-971; Aug. 3, 2004.
Gleave, "A Versatule Binary Vector System with a T-DNA Organisational Structure . . ." *Plant Molecular Biology* vol. 20; pp. 1203-1207;Apr. 1, 1992.
Hooykaas et al., "*Agrobacterium* and Plant Genetic Engineering," *Plant Molecular Biology* vol. 18; pp. 15-38; 1992.
Jorgensen et al., "Chalcone Synthase Cosuppression Phenotypes in Petunia Flowers: Comparison of Sense vs. Antisense Constructs and Single-Copy vs. Complex T-DNA Sequences," *Plant Molecular Biology* vol. 31; pp. 957-973; 1996.
Krizkova et al., "Direct repeats of T-DNA integrated in tobacco chromosome: characterization of junction regions," *Plant J*, vol. 16(6), pp. 673-680; 1998.
Kunik et al., "Genetic transformation of HeLa cells by Agrobacterium," *Proceedings of National Academy of Science*, vol. 48, pp. 1871-1876; Feb. 13, 2001.
Lewis et al., "Palindromic DNA and Genome Stability: Further Studies," *Annals of the New York Academy of Sciences* vol. 870; pp. 45-47; 1999.

(Continued)

*Primary Examiner* — Anne Kubelik
(74) *Attorney, Agent, or Firm* — Dentons US LLP; Amanda Carmany-Rampey, Esq.

(57) ABSTRACT

Methods of providing gene suppression DNA in a eukaryotic organism comprising introducing a first DNA segment and at least one second DNA segment into the genome of the organism. One of the DNA segments contains a promoter and a transcribable DNA. Another DNA segment contains at least part of the transcribable DNA. When inserted in tandem, the DNA segments are assembled in vivo forming a recombinant transcription unit. RNA transcribed from the transcription unit can form double-stranded RNA.

20 Claims, 3 Drawing Sheets

(56) References Cited

OTHER PUBLICATIONS

Mette et al., "Transcriptional silencing and promoter methylation triggered by double-stranded RNA," *The EMBO Journal* vol. 19, No. 19; pp. 5194-5201; 5199; 5200; Oct. 2, 2000.
Michielse et al., "Agrobacterium-mediated transformation as a tool for functional genomics in fungi," *Fungal Genetics and Biology* vol. 48; pp. 1-17; Aug. 3, 2004.
Que et al., "The Frequency and Degree of Cosuppression by Sense Chalcone Synthase Transgenes are Dependent on Transgene Promoter Strength and are Reduced by Premature Nonsense Codons in the Transgene Coding Sequence," *The Plant Cell* vol. 9; pp. 1357-1368; 1997.
Stam et al., "Distinct Features of Post-Transcriptional Gene Silencing by Antisense Transgenes in Single Copy and Inverted T-DNA Repeat Loci," *The Plant Journal* vol. 21(1); pp. 27-42; 2000.
Stam et al., "Position-Dependent Methylation and Transcriptional Silencing of Transgenes in Inverted T-DNA Repeats: Implications for Posttranscriptional Silencing of Homologous Host Genes in Plants," *Molecular and Cellular Biology* vol. 18(11); pp. 6165-6177; 1998.
Vaucheret et al., "Post-Transcriptional Gene Silencing in Plants," *Journal of Cell Science* vol. 114; pp. 3083-3091; 2001.

\* cited by examiner arrow indicates orientation relative to a native transcription

IN VIVO ASSEMBLY OF TRANSCRIPTION UNITS

This application is a continuation of U.S. Ser. No. 14/109,835, filed Dec. 17, 2013, which is a continuation of U.S. Ser. No. 11/057,071, filed Feb. 11, 2005, now U.S. Pat. No. 8,609,934, which claims the priority of U.S. Provisional Application Ser. No. 60/544,690 filed Feb. 13, 2004, the entire disclosures of which are incorporated herein by reference in their entireties.

FIELD OF THE INVENTION

Disclosed herein are methods of assembling transcription units in a cell and plasmid vectors for in vivo assembly of transcription units for gene suppression.

BACKGROUND

In some cases a desired insertion of a recombinant transcription unit into an organism may be limited by patent rights, e.g. directed to vectors comprising the transcription unit or methods using the transcription unit. Some of such limitations may be avoided by in vivo assembly of transcription units, e.g. in the field of gene suppression.

Gene suppression may be effective against a native gene associated with a trait in a plant or animal, e.g. to provide reduced levels of a protein encoded by the native gene and might lead to altered levels of the corresponding substrate and metabolites. Gene suppression can also be effective against target genes in pest or pathogen organisms, e.g. a virus, insect or nematodes that may feed on or infect an organism containing gene suppression agents. Gene suppression includes any of the well-known methods for suppressing transcription of a gene or the accumulation of the mRNA corresponding to that gene, thereby preventing translation of the transcript into protein.

More particularly, gene suppression mediated by inserting a recombinant DNA construct with anti-sense oriented DNA to regulate gene expression in plant cells is disclosed in U.S. Pat. No. 5,107,065 (Shewmaker et al.) and U.S. Pat. No. 5,759,829 (Shewmaker et al.). Plants transformed using such anti-sense oriented DNA constructs for gene suppression can comprise integrated DNA arranged as an inverted repeat that resulted from co-insertion of several copies of the transfer DNA (T-DNA) into plants by *Agrobacterium*-mediated transformation, as disclosed by Redenbaugh et al. in "Safety Assessment of Genetically Engineered Flaw Savr™ Tomato, CRC Press, Inc. (1992). Inverted repeat insertions can comprise a part or all of the T-DNA, e.g. contain an inverted repeat of a complete or partial anti-sense construct. Screening for inserted DNA comprising inverted repeat elements can improve the efficiency of identifying transformation events effective for gene silencing when the transformation construct is a simple anti-sense DNA construct.

Gene suppression triggered by inserting a recombinant DNA construct with sense-oriented DNA to regulate gene expression in plants is disclosed in U.S. Pat. No. 5,283,184 (Jorgensen et al.) and U.S. Pat. No. 5,231,020 (Jorgensen et al.). Inserted T-DNA providing gene suppression in plants transformed with such sense constructs by *Agrobacterium* is organized predominately in inverted repeat structures, as disclosed by Jorgensen et al., Mol. Gen. Genet., 207: 471-477 (1987). See also Stam et al., The Plant Journal, 12: 63-82 (1997) and De Buck et al., Plant Mol. Biol. 46 433-445 (2001), who used segregation studies to support Jorgensen's finding that in many events gene silencing is mediated by multimeric transgene T-DNA where the T-DNAs are arranged in inverted repeats. Screening for inserted DNA comprising inverted repeat elements can improve the gene silencing efficiency when transforming with simple sense-orientated DNA constructs.

Gene silencing can also be effected by transcribing RNA from both a sense and an anti-sense oriented DNA using two separate transcription units, e.g. as disclosed by Shewmaker et al. in U.S. Pat. No. 5,107,065 where in Example 1 a binary vector was prepared with both sense and anti-sense aroA genes. Similar constructs are disclosed in International Publication No. WO 99/53050 (Waterhouse et al.). See also U.S. Pat. No. 6,326,193 where gene targeted DNA is operably linked to opposing promoters.

Gene suppression can be achieved in plants by providing transformation constructs that are capable of generating an RNA that can form double-stranded RNA along at least part of its length. Gene suppression in plants is disclosed in EP 0426195 A1 (Goldbach et al.) where recombinant DNA constructs for transcription into hairpin RNA provided transgenic plants with resistance to tobacco spotted wilt virus. See also Sijen et al., The Plant Cell, Vol. 8, 2277-2294 (1996) which discloses the use of constructs carrying inverted repeats (sense followed by anti-sense) of a cowpea mosaic virus gene in transgenic plants to mediate virus resistance. See also International Publication No. 98/53083 (Grierson et al.) and related U.S. Patent Application Publication No. 2003/0175965 A1 (Lowe et al.) which disclose gene suppression, using a double stranded RNA construct comprising a gene coding sequence preceded by an inverted repeat of 5'UTR. Constructs for posttranscriptional gene suppression in plants by double-stranded RNA of the target gene are also disclosed in International Publications WO 99/53050 (Waterhouse et al.) and WO 99/49029 (Graham et al.). See also U.S. Patent Application Publication No. US 2002/0048814 A1 (Oeller) where DNA constructs are transcribed to sense or anti-sense RNA with a hairpin-forming poly(T)-poly(A) tail. See also U.S. Patent Application Publication US 2003/0018993 A1 (Gutterson et al.) where sense or anti-sense DNA is followed by an inverted repeat of the 3' untranslated region of the NOS gene. See also U.S. Patent Application Publication No. US 2003/0036197 A1 (Glassman et al.) where RNA for reducing the expression of target mRNA comprises a part with homology to target mRNA and a part with complementary RNA regions that are unrelated to endogenous RNA.

The production of dsRNA in plants to inhibit gene expression, e.g. in a nematode feeding on the plant, is disclosed U.S. Pat. No. 6,506,559 (Fire et al.). Multi-gene suppression vectors for use in plants are disclosed in U.S. patent application Ser. No. 10/465,800 (Fillatti).

All of the above-described patents, applications and international publications disclosing materials and methods for gene suppression in plants using recombinant DNA constructs are incorporated herein by reference.

Transcriptional suppression such as promoter trans suppression can be effected by expressing a DNA construct comprising a promoter operably linked to inverted repeats of promoter DNA from a target gene as disclosed by Mette et al., The EMBO Journal, Vol. 18, pp. 241-148, (1999) and by Mette et al., The EMBO Journal, Vol. 19, pp. 5194-5201-148, (2000), both of which are incorporated herein by reference.

Known methods for in vivo modification of recombinant DNA include homologous recombination and site-specific recombination. For instance, U.S. Pat. No. 6,750,379 discloses homologous recombination-mediated transgene alterations in plants, e.g. for marker deletion. Site-specific recombination of DNA in plant cells is disclosed in U.S. Pat. No. 5,658,772 and International Publications WO 02/088369 A1 and WO 2004/067749 A1. See also WO 2004/067748 A1 which discloses post transcription assembly by splicing of an artificial intron from transcribed RNA.

Co-integration studies of T-DNA are discussed by Krizkova et al. in Plant J., 16, 673-680 (1998) which reports assembling of a transcription unit from two copies of a T-DNA which has a promoterless gene at the 3' end and an unlinked promoter at the 5' end.

SUMMARY OF THE INVENTION

This invention provides methods of assembling in vivo a recombinant transcription unit for gene suppression from parts of the recombinant transcription unit. When parts of a transcription unit are inserted in tandem, e.g. into the genome of a eukaryotic organism, the parts form an assembled transcription unit comprising a promoter DNA and transcribable DNA that is capable of forming double-stranded RNA.

Aspects of the invention can be illustrated by a specific embodiment in which a transcription unit for suppression of a gene is assembled in vivo from two segments of DNA. With reference to FIG. 1, an organism can be transformed using a plasmid vector with two T-DNA segments. The first segment comprises promoter DNA and transcribable DNA from the gene targeted for suppression, say in a sense orientation; and, the second segment comprises the same transcribable DNA but in an anti-sense orientation, e.g. with respect to a polyadenylation site DNA. When the two segments of DNA are inserted in tandem in a host organism the assembled transcription unit comprises promoter DNA operably linked to sense-oriented and anti-sense-oriented DNA from the gene targeted for suppression which can be transcribed to RNA capable of forming double-stranded RNA effective for suppression of the targeted gene.

More generally, the method comprises introducing into a chromosome in a cell a first segment of DNA and a distinct second segment of DNA each comprising a part of a transcription unit where a first segment of DNA comprises a promoter DNA and transcribable DNA from at least one gene target for suppression in either a sense or and antisense orientation and where a second segment of DNA comprises at least a part of the transcribable DNA. In the methods of the invention the segments of DNA are inserted in tandem into a chromosome in a cell to form the assembled transcription unit comprising the promoter DNA operably linked to transcribable DNA from the first segment of DNA linked to transcribable DNA from the second segment of DNA. The transcribable DNA in the segments are oriented so that RNA transcribed from the assembled transcription unit is capable of forming double-stranded RNA. The method further comprises selecting for a transgenic cell in which double-stranded RNA is produced.

In one embodiment of the method, the first segment of DNA comprises a promoter DNA and DNA from at least one gene targeted for suppression in an anti-sense orientation with respect to transcription initiated by the promoter. In another embodiment of the method, at least one of the first and second segments of DNA further comprises a selectable marker transcription unit. Although the two segments of DNA can be introduced from separate plasmids, in preferred aspects of the invention, first and second segments of DNA are introduced from a single plasmid.

When a selectable marker transcription unit is included, e.g. in one of the segments of DNA, the selectable marker can impart herbicide or antibiotic resistance. For example when the transformed organism is a plant, transformation events comprising inserted DNA can be selected on an herbicide-containing medium or on an antibiotic-containing medium. In other embodiments the methods can further comprise introducing a third segment of DNA comprising a selectable marker transcription unit. More particularly, the third segment of DNA is introduced from a second plasmid such as a Ti plasmid in a binary vector system of *Agrobacterium tumefaciens*-mediated transformation.

When the first and second segments of DNA are introduced from a single plasmid, a preferred method of the invention is where the first and second segments of DNA are T-DNAs which are co-integrated into the genome of a eukaryotic organism by *Agrobacterium tumefaciens*-mediated transformation using a plasmid vector comprising the two T-DNAs. Such a plasmid vector for gene suppression comprises (a) a first T-DNA comprising, between left and right T-DNA borders, a promoter which is operable in said eukaryotic organism operably linked to DNA from at least one gene targeted for suppression;

(b) a second T-DNA comprising, between left and right T-DNA borders, at least part of said DNA from at least one gene targeted for suppression.

Although any combination of left and right T-DNA borders is effective, in one embodiment of the invention, the DNA from one or more genes targeted for suppression in the first T-DNA is located adjacent to a right T-DNA border and at least part of said DNA from one or more genes targeted for suppression in the second T-DNA is located adjacent to a right T-DNA border. In a preferred embodiment of the method, the DNA from one or more genes targeted for suppression in the first T-DNA is in an anti-sense orientation with respect to transcription initiated by the promoter.

In still another aspect of the invention each of the T-DNAs can contain a common DNA of identical sequence adjacent to the T-DNA borders where the common DNA is oriented in each T-DNA to enable annealing of the T-strands produced from the two T-DNAs. Such annealing allows the borders to be eliminated from the assembled transcription unit.

This invention also provides plasmid vectors for *Agrobacterium tumefaciens*-mediated, tandem co-integration of two T-DNAs into the genome of a plant for in vivo assembly of gene suppression transcription unit. In such a plasmid vector a first T-DNA comprises, in series, a promoter which is operable in a plant, DNA from at least one gene targeted for suppression and a T-DNA border and a second T-DNA comprises, in series, a T-DNA border and at least a part of said DNA from at least one gene targeted for suppression. When the first and second T-DNAs are co-integrated in tandem and joined at the T-DNA borders, a transcription unit is formed comprising said promoter operably linked to DNA from at least one gene targeted for suppression. And, RNA transcribed by such a transcription unit can form double-stranded RNA.

Such plasmid vectors can further comprise a marker transcription unit in at least one of the T-DNAs. For instance, when a plasmid vector of this invention is used to assemble a gene suppression transcription unit in a plant, a marker transcription unit in one of the T-DNAs will express a marker gene that allows selection of transgenic events on a medium containing an appropriate herbicide or an antibiotic compound. Useful herbicides for selection are in the group consisting of a glyphosate herbicide, a phosphinothricin herbicide, an oxynil herbicide, an imidazolinone herbicide, a dinitroaniline herbicide, a pyridine herbicide, a sulfonylurea herbicide, a bialaphos herbicide, a sulfonamide herbicide and a gluphosinate herbicide. Useful antibiotics are in the group consisting of kanamycin, gentomycin, hygromycin and bleomycin.

T-DNA used in *Agrobacterium*-mediated insertion typically employs both a left and a right T-DNA border. Multiple insertions can occur with adjoining DNA from T-DNA borders. The T-DNAs can be designed so that desired tandem insertion occurs at a right border-right border junction (RB-RB), a left border-left border junction (LB-LB) or at a right border-left border junction (RB-LB). Analysis of the junction, e.g. by hybridization assay of an amplified border junction, can facilitate selection of an intended assembly of a transcription unit.

When it is desired to assemble a transcription unit without internal T-DNA border elements, the T-DNA border elements at the junction of the T-DNAs can be excised by employing adjacent to the T-DNA elements a common DNA of identical sequence in the above-described manner. A plasmid vector with such a common DNA adjacent to borders is a useful embodiment of this invention. This invention also provides plasmid vectors in which the DNA from one or more genes targeted for suppression in the first T-DNA is in an anti-sense orientation with respect to transcription initiated by the promoter.

An especially useful aspect of this invention is a method of in vivo assembling of a recombinant transcription unit for gene suppression from two T-DNAs which are co-integrated in tandem into the genome of a eukaryotic organism by *Agrobacterium tumefaciens*-mediated transformation using a binary plasmid vector comprising two T-DNAs. This method comprises introducing into a cell of an organism a binary plasmid vector comprising two T-DNAs and a tumor-inducing plasmid. A first T-DNA in such a binary plasmid vector comprises, in series, a promoter, transcribable DNA from at least one gene targeted for suppression in an anti-sense orientation and a T-DNA border and a second T-DNA comprises, in series, a T-DNA border and at least a part of the transcribable DNA in a sense orientation with respect to the border. When they are inserted in tandem into the chromosome, the first and second T-DNAs can form an assembled transcription unit comprising the promoter operably linked to transcribable DNA from the first T-DNA linked to T-DNA border, e.g. border from both T-DNAs, linked to transcribable DNA from the second T-DNA. The RNA transcribed from the assembled transcription unit is capable of forming double-stranded RNA. The method further comprises selecting a transgenic cell in which the double-stranded RNA is produced. This method is especially useful in plant transformation and when one of the T-DNAs contains a marker transcription unit.

BRIEF DESCRIPTION OF THE DRAWINGS

FIG. 3 also specifically illustrates assembly using annealer DNA.

DETAILED DESCRIPTION

Figure 1:
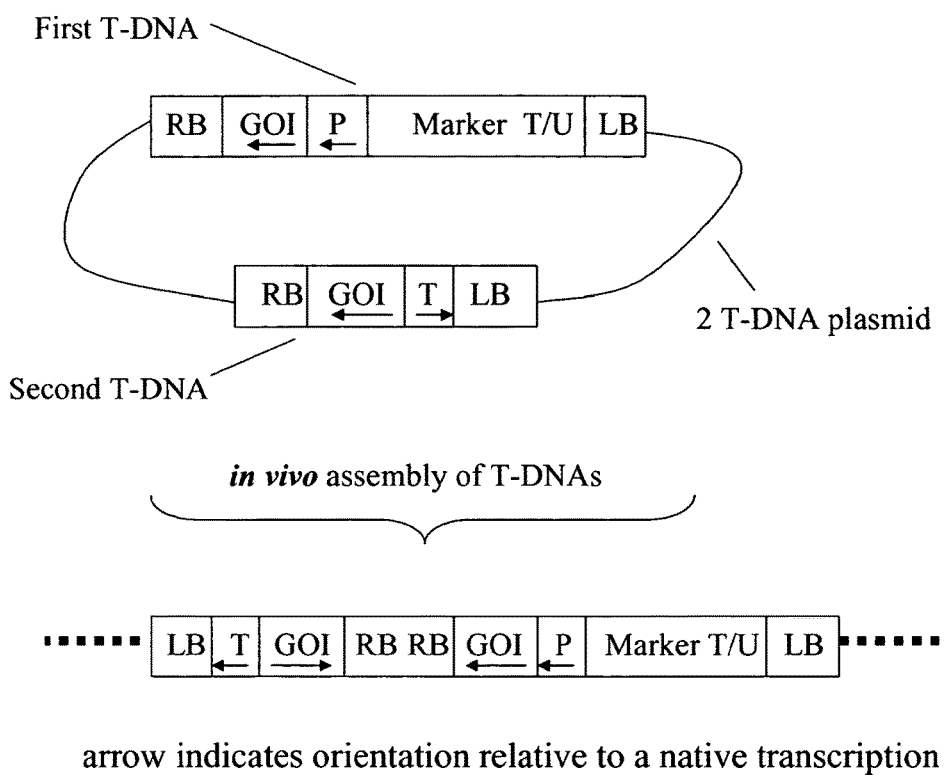
FIG. 1 is a schematic illustration of elements of a plasmid vector of this invention and its use in tandem co-integration of two T-DNAs.

As used herein "transfer DNA" (T-DNA) means DNA which integrates into a genome by *Agrobacterium*-mediated transformation. For *Agrobacterium*-mediated transformation T-DNA is typically the part of a binary plasmid vector, which is flanked by T-DNA borders, and the binary vector is transferred into an *Agrobacterium tumefaciens* strain carrying a disarmed tumor inducing (Ti) plasmid.

As used herein, "T strands" refer to the free linear single-stranded copies of the T-DNA region generated during the T-DNA transfer process of *A. tumefaciens*.

As used herein, "gene" refers to a segment of DNA which carries all the information for transcribing a RNA encoding a protein. The gene encompasses a 5' promoter region associated with the transcriptional activity of the gene, any intron and exon regions and 3' and 5' untranslated regions ("UTR") associated with the transcript and a transcriptional termination region. It is well known in the art that RNA having a double-stranded form which is transcribed from DNA of a gene targeted for suppression will be effective in suppressing that gene. Transcribable DNA for such suppression can comprise any part of the DNA of a gene targeted for suppression. In many cases the target DNA segment is preferably specific to a single target gene. In other cases, when multiple gene suppression is desired, it may be useful to select a target DNA segment, which has homology to the DNA of more than one target gene or sequential DNA from multiple genes.

As used herein "vector" means a DNA molecule capable of replication in a host cell and/or to which another DNA segment can be operatively linked so as to bring about replication of the attached segment. Preferred vectors for *Agrobacterium*-mediated transformation are plasmid vectors in which segments of DNA intended to be transferred to the plant cell are flanked by a right and a left T-DNA border.

As used herein "transgenic" refers to an organism, e.g. plant, or differentiated part of an organism, e.g. a seed, whose genome has been altered by the incorporation of recombinant DNA comprising exogenous genetic material or additional copies of native genetic material, e.g. by transformation or recombination of the organism or an ancestral organism.

As used herein, "a transgenic plant" is any plant that stably incorporates a transgene in a manner that facilitates transmission of that transgene to progeny, e.g. by any sexual or asexual method. Transgenic plants include progeny plants of an original plant derived from a transformation process including progeny of breeding transgenic plants with wild type plants or other transgenic plants. Crop plants of particular interest in the present invention include, but are not limited to maize, soybean, cotton, canola (rape), wheat, rice, sunflower, safflower and flax. Other crops of interest include plants producing vegetables, fruit, grass and wood.

As used herein "tandem" refers to the adjacent integration of DNAs into a genome, e.g. where two DNAs are inserted such that there is little or no non-transgenic DNA sequence between them.

As used herein "transcription unit" means a segment of DNA comprising at least a promoter DNA and transcribable DNA. Although not required, transcription units for gene expression typically also have a polyadenylation signal and polyadenylation site to allow transcribed DNA to be transported from the nucleus. Such polyadenylation signal and polyadenylation site is commonly called a terminator. As is illustrated in FIG. 1, a "marker T/U" designates a marker gene transcription unit, e.g. promoter, marker gene protein-encoding DNA and transcription terminator. Assemble transcription units of this invention will comprise promoter DNA and transcribable DNA from at least one gene targeted for suppression in both a sense and anti-sense orientation.

In practice, DNA is stably integrated into only a small percentage of target cells following transformation. Marker genes are used to provide an efficient system for identification of those cells that are stably transformed by receiving and integrating a transgenic DNA construct into their genomes. Preferred marker genes provide selective markers, which confer resistance to a selective agent, such as an antibiotic or herbicide. Any of the herbicides to which plants of this invention may be resistant are useful agents for selective markers. Potentially transformed cells are exposed to the selective agent. In the population of surviving cells will be those cells where, generally, the resistance-conferring gene is integrated and expressed at sufficient levels to permit cell survival. Cells may be tested further to confirm stable integration of the transgenic DNA. Commonly used selective marker genes include those conferring resistance to antibiotics such as kanamycin (nptII), hygromycin B (aph IV) and gentamycin (aac3 and aacC4) or bleomycin. Other selective marker genes produce a protein that provides resistance to herbicides in the transgenic organism. Such a selective marker allows selection of transgenic events on a medium containing an herbicide selected from the group consisting of a glyphosate herbicide, a phosphinothricin herbicide, an oxynil herbicide, an imidazolinone herbicide, a dinitroaniline herbicide, a pyridine herbicide, a sulfonylurea herbicide, a bialaphos herbicide, a sulfonamide herbicide and a gluphosinate herbicide. Examples of such selectable markers are illustrated in U.S. Pat. Nos. 5,550,318; 5,633,435; 5,780,708 and 6,118,047, all of which are incorporated herein by reference. Screenable markers which provide an ability to visually identify transformants can also be employed, e.g., a gene expressing a colored or fluorescent protein such as a luciferase or green fluorescent protein (GFP) (U.S. Pat. No. 5,491,084, herein incorporated by reference) or a gene expressing a beta-glucuronidase or uidA gene (GUS) (U.S. Pat. No. 5,599,670, herein incorporated by reference) for which various chromogenic substrates are known.

Recombinant DNA Constructs for Plant Transformation

Recombinant DNA constructs of this invention for producing gene suppression agents in transgenic plants can be readily prepared by those skilled in the art following the guidance disclosed herein. With reference to FIG. 1, typically, such a recombinant DNA construct comprises a binary vector for *Agrobacterium*-mediated transformation comprising two T-DNAs (designated as "2 T-DNA plasmid") where each of the T-DNAs comprise elements of a part of a gene suppression transcription unit. Each T-DNA is flanked by border elements from an *Agrobacterium tumefaciens* tumor-inducing plasmid. Such border elements are designated as left border (LB) and right border (RB) elements. Additional DNA forming the plasmid is indicated by the lines connecting the T-DNAs. A first T-DNA in such a 2 T-DNA plasmid comprises between left and right border elements a marker transcription unit (marker T/U), a promoter element (P) and transcribable DNA from a gene targeted for suppression (GOI). A second T-DNA in such a 2 T-DNA plasmid comprises between left and right borders transcribable DNA from the gene targeted for suppression (GOI) and an optional transcription terminator (T). The GOI segment in the T-DNAs contains at least some of the same sequence to allow transcribed RNA to from a double strand. In FIG. 1 the arrows indicate functional (sense/anti-sense) orientation of the DNA with respect to native transcription of the DNA. In an alternative embodiment the polarity, i.e. sense/anti-sense orientations, of the transcribable DNA can be reversed. In yet other embodiments the DNA from the gene targeted for suppression can be in but one of the T-DNAs where each of the T-DNAs further contains DNA that can be transcribed to hybridizing RNA.

During *Agrobacterium tumefaciens*-mediated transformation of a host plant a percentage of the transgenic events will have the two T-DNAs integrated in tandem (Redenbaugh et al. in "Safety Assessment of Genetically Engineered Flaw Savr™ Tomato, CRC Press, Inc. (1992)). Tandem integration of two T-DNAs can occur in four ways: left border to left border, right border to right border, and two different arrangements of a left border to a right border. In the preferred orientation of the tandem T-DNAs, the transcribable DNA segments from a gene targeted for suppression are inverted with respect to each other in the assembled transcription unit, i.e. one target DNA segment is in a sense orientation and the other is in an anti-sense orientation relative to transcription from promoter P. In particular, when a two T-DNA plasmid is constructed as illustrated in FIG. 1, a right border to right border tandem insertion will result in the in vivo assembly of a transcription unit. Transcription of the in vivo assembled transcription unit will provide RNA that can form at least a stretch of double-stranded RNA from the transcribable DNA from a gene targeted for suppression.

In the case of plant transformation tissue, e.g. shoots or callus, transformed with two in-vivo-assembling T-DNAs can be screened for the presence of both T-DNAs in the preferred in vivo-assembling tandem configuration using PCR or other gene mapping methods, e.g. DNA or RNA hybridization such as a Southern or Northern hybridization. PCR reaction can be run using one primer from the first T-DNA and a second primer from the second T-DNA. Only transgenic shoots with the predicted configuration would be transferred to the greenhouse for seed production.

Recombinant DNA constructs, e.g. plasmid vectors comprising two T-DNAs, can be assembled using commercially available materials and methods known to those of ordinary skill in the art.

Depending on the application the, promoter used to drive the gene suppression construct may be constitutive, preferably expressed in particular tissues or at particular development stages or inducible. See U.S. Pat. Nos. 5,858,742 and 5,322,938 which disclose versions of the constitutive promoter derived from cauliflower mosaic virus (CaMV35S), U.S. Pat. No. 5,641,876 which discloses a constitutive rice actin promoter, U.S. Pat. No. 6,429,357 which discloses a constitutive rice actin 2 promoter and intron and U.S. Pat. No. 6,177,611 which discloses constitutive maize promoters. See U.S. Pat. Nos. 5,837,848; 6,437,217 and 6,426,446 which disclose root-specific promoters and U.S. Pat. No. 6,433,252 which discloses a maize L3 oleosin promoter. See also U.S. Pat. No. 6,084,089 which discloses cold inducible promoters, U.S. Pat. No. 6,294,714 which discloses light-inducible promoters, U.S. Pat. No. 6,140,078 which discloses salt-inducible promoters, and U.S. Pat. No. 6,252,138 which discloses pathogen-inducible promoters. Examples of seed-specific promoters include the 5' regulatory regions from such genes as napin (Kridl et al., *Seed Sci. Res.* 1:209-219 (1991)), phaseolin (Bustos et al., *Plant Cell,* 1(9):839-853 (1989)), soybean trypsin inhibitor (Riggs et al., *Plant Cell* 1(6):609-621 (1989)), ACP (Baerson et al., *Plant Mol. Biol.,* 22(2):255-267 (1993)), stearoyl-ACP desaturase (Slocombe et al., *Plant Physiol.* 104(4):167-176 (1994)), soybean a' subunit of b-conglycinin (soy 7s, (Chen et al., *Proc. Natl. Acad. Sci.,* 83:8560-8564 (1986))), soybean a subunit of b-conglycinin (U.S. Pat. No. 6,825,398), and oleosin (see, for example, Hong et al., *Plant Mol. Biol.,* 34(3):549-555 (1997). All of the above-described patents disclosing promoters and their use in recombinant DNA constructs in plants are incorporated herein by reference.

Transformation Methods and Transgenic Plants—

Methods and compositions for transforming plants by introducing recombinant DNA into a plant genome in the practice of this invention can include any of the well-known and demonstrated methods. A preferred method of plant transformation is microprojectile bombardment as illustrated in U.S. Pat. No. 5,015,580 (soy), U.S. Pat. No. 5,550,318 (corn), U.S. Pat. No. 5,538,880 (corn), U.S. Pat. No. 6,153,812 (wheat), U.S. Pat. No. 6,160,208 (corn), U.S. Pat. No. 6,288,312 (rice) and U.S. Pat. No. 6,399,861 (corn). Another preferred method of plant transformation is Agrobacterium-mediated transformation as illustrated in U.S. Pat. No. 5,159,135 (cotton), U.S. Pat. No. 5,824,877 (soy), U.S. Pat. No. 5,591,616 (corn) and U.S. Pat. No. 6,384,301 (soy). All of the above-described patents disclosing materials and methods for plant transformation are incorporated herein by reference.

Transformation methods of this invention to provide plants with recombinant DNA constructs for effecting gene suppression are preferably practiced via tissue culture on media and in a controlled environment. "Media" refers to the numerous nutrient mixtures that are used to grow cells in vitro, that is, outside of the intact living organism. Recipient cell targets include, but are not limited to, meristem cells, callus, immature embryos, hypocotyls explants, cotyledon explants, leaf explants, and gametic cells such as microspores, pollen, sperm and egg cells. It is contemplated that any cell from which a fertile plant may be regenerated is useful as a recipient cell. Callus may be initiated from tissue sources including, but not limited to, immature embryos, seedling apical meristems, microspores and the like. Those cells, which are capable of proliferating as callus, also are recipient cells for genetic transformation. Practical transformation methods and materials for making transgenic plants of this invention, e.g. various media and recipient target cells, transformation of immature embryos and subsequent regeneration of fertile transgenic plants to produce transgenic seed for propagating transgenic plants are disclosed in U.S. Pat. Nos. 6,194,636; 6,232,526; 6,541,682 and 6,603,061 and U.S. Patent Application publication US 2004/0216189 A1, all of which are incorporated herein by reference.

The seeds of transgenic plants can be harvested from fertile transgenic plants and used to grow progeny generations of transformed plants of this invention including hybrid plants line comprising the recombinant DNA construct expressing an agent for gene suppression.

In addition to direct transformation of a plant with a recombinant DNA construct, transgenic plants can be prepared by crossing a first plant having a recombinant DNA construct with a second plant lacking the construct. For example, recombinant DNA can be introduced into a plant line that is amenable to transformation to produce a transgenic plant which can be crossed with a second plant line to introgress the recombinant DNA into the second plant line.

A transgenic plant with recombinant DNA effecting gene suppression can be crossed with plant line having other recombinant DNA that confers another trait, e.g. yield improvement, herbicide resistance or pest resistance to produce progeny plants having recombinant DNA that confers both gene suppression and the other trait. Typically, in such breeding for combining traits the transgenic plant donating the additional trait is a male line and the transgenic plant carrying the base traits is the female line. The progeny of this cross will segregate such that some of the plants will carry the DNA for both parental traits and some will carry DNA for one parental trait; such plants can be identified by markers associated with parental recombinant DNA. Progeny plants carrying DNA for both parental traits can be crossed back into the female parent line multiple times, e.g. usually 6 to 8 generations, to produce a progeny plant with substantially the same genotype as one original transgenic parental line but for the recombinant DNA of the other transgenic parental line.

The constructs and methods of this invention can be used to provide transgenic plants transcribing dsRNA for gene suppression. When gene suppression is for modifying oil, contemplated transgenic plants include corn, soybean, canola, sunflower, safflower, cotton and the like. When gene suppression is for pest control, e.g. the double-stranded RNA agent is targeted to a plant pest, contemplated transgenic plants include corn, soybean, wheat, potato, cotton and fruit. When fruit or seed quality or composition is an object of gene suppression, contemplated transgenic plants include corn, soybean, canola, cotton, wheat, rice, rapeseed, sugar beet, potato, and fruit.

Example 1

This example illustrates the design of a 2 T-DNA plasmid vector for in vivo assembly of a recombinant transcription unit, which can be used to suppress an endogenous plant gene. With reference to FIG. 1, a plasmid vector is prepared with two T-DNAs, each flanked by Agrobacterium T-DNA border elements, i.e. right border DNA (RB) and left border DNA (LB).

The first T-DNA comprises a left T-DNA border (LB), a transgenic insertion-selectable marker (Marker T/U) for glyphosate herbicide resistance, a promoter (P) functional in plants, transcribable DNA from a gene targeted for suppression (GOI) and right T-DNA border (RB), schematically represented in FIG. 1 as "RB-GOI-P-Marker T/U-LB". More specifically, the Marker T/U comprises a constitutive promoter derived from a figwort mosaic virus (eFMV) operably linked to a 5-enolpyruvylshikimate-3-phosphate synthase gene (as disclosed in U.S. Pat. No. 5,627,061 (Barry, et al.), U.S. Pat. No. 5,633,435 (Barry, et al.), and U.S. Pat. No. 6,040,497 (Spencer, et al.)) and polyadenylation DNA. More specifically, the promoter (P) is a soybean (G. max) 7Sa' promoter (P) and the transcribable DNA from a gene targeted for suppression (GOI) is substantially all of intron 1 of the soybean (G. max) FAD2-1A gene (as disclosed in U.S. Patent Application Publication U.S. 2004/0006792 A1). Although either orientation can be used, in this example the targeted gene DNA (GOI) is in a sense orientation with respect to promoter P.

The second T-DNA contains a left and right T-DNA border between which there is polyadenylation DNA (T) from a bacterial NOS gene and transcribable DNA from the soybean FAD2-1A gene targeted for suppression. The transcribable DNA is in an anti-sense orientation with respect to the polyadenylation DNA. As shown in FIG. 1, the second T-DNA is schematically illustrated as "RB-GOI-T-LB". The polyadenylation DNA (T) is not a required element.

Example 2

This example illustrates the design of a 2 T-DNA plasmid vector for in vivo assembly of a recombinant transcription unit to suppress two endogenous plant genes. The plasmid vector is prepared as described in Example 1 except that the GOI in each T-DNA comprises DNA from the soybean (G.

*max*) genes FAD2 and FAD3 (as disclosed in U.S. Patent Application Publication No. 2004/0006792 A1). The 3' 300 bp of the intron of soy FAD2-1A, together with intron 4 of soy FAD3A, were combined and placed under the seed-specific promoter 7Sa', and cloned into the in vivo assembly vector as described in Example 1. In addition, for over expression purposes, the *Cuphea puclcherrima* KASIV (U.S. Patent Application Publication No. 2003/00635822 A1), driven by the eUSP88 promoter (U.S. Patent Application Publication No. 2003/00229918 A1), and *Ricinus communis* delta 9 desaturase (U.S. Pat. No. 5,723,595), driven by the promoter 7Sa, were inserted into the T-DNA 1, resulting in a plasmid vector denoted pMON83539.

A second vector, denoted pMON83542, which targeted suppression of FAD2, FAD3A and FATB (WO04000871A2) demonstrated the use of the 3'UTR fragments, instead of introns, in the suppression cassette.

Example 3

This example illustrates plant transformation using the 2 T-DNA plasmid vectors prepared in Example 2. The vectors were introduced into soybean callus using *Agrobacterium*-mediated transformation methods as described by Martinell in U.S. Pat. No. 6,384,301. Transformed soybean cells were identified as containing the first T-DNA by selection on a medium containing glyphosate herbicide. Subsequently, the genomes of transformed plant cells were screened for concurrent tandem insertion of the first T-DNA and the second T-DNA, i.e. in the "right border to right border" assembly, as shown in FIG. 1. This screening was done by Southern hybridization mapping methods. Alternatively, PCR methods could be used for screening. Transformed soybean plants containing the preferred configuration in their genome were transferred to a greenhouse for seed production.

For example, leaf tissue was taken from the R0 plants transformed with plasmid vector pMON83539 and Southern analysis was performed. Probes and restriction enzyme digests were chosen in order to identify events containing a right-border-right border assembly of both T-DNAs. Approximately 25% of all transformants had properly assembled RB-RB T-DNAs.

Fatty acid composition analysis of seeds produced from transgenic soybean plants was performed using gas chromatography to identify methyl esters of fatty acid compounds extracted from seed. Mature R1 seeds from soybean transformed with plasmid vector pMON83539 were harvested and the fatty acid composition of single seeds was determined. R1 seeds of each event were segregating for the transgenes and yielded seeds with conventional soybean composition, as well as modified versions. Almost all events with the assembled 2 T-DNAs had significantly elevated oleic acid (18:1). Table 1 shows the fatty acid composition of the seed with the highest oleic acid from each of the in vivo-assembled events. The oleic acid level of null seeds, e.g. negative segregants, is shown below the values for seeds from plants indicating positive for an assembled gene suppression transcription unit. Soybean plants transformed with plasmid vector pMON83539 exhibited increased oleic acid indicating suppression of the FAD2 gene. The analysis of the R1 seeds from soybean transformed with plasmid vector pMON83542, which used the 3'UTR fragments, also demonstrated increased oleic acid.

TABLE 1

| Single seeds per event | Oleic acid, % |
|---|---|
| pMON83539 GM_A62564 - POS | 84.7 |
| pMON83539 GM_A65463 - POS | 82.7 |
| pMON83539 GM_A65686 - POS | 75.5 |
| pMON83539 GM_A65462 - POS | 73.4 |
| pMON83539 GM_A65956 - POS | 72.3 |
| pMON83539 GM_A65437 - POS | 70.9 |
| pMON83539 GM_A65456 - POS | 70.2 |
| pMON83539 GM_A65709 - POS | 63.9 |
| pMON83539 GM_A65427 - POS | 58.2 |
| pMON83539 GM_A62571 - POS | 55.6 |
| pMON83539 GM_A65689 - POS | 53.1 |
| pMON83539 GM_A65462 - Null | 19.7 |
| pMON83539 GM_A65462 - Null | 18.7 |
| pMON83542 GM_A67727 - POS | 73.8 |
| pMON83542 GM_A65846 - POS | 70.1 |
| pMON83542 GM_A67706 - POS | 67.5 |
| pMON83542 GM_A67712 - POS | 65.3 |
| pMON83542 GM_A67735 - POS | 63.5 |
| pMON83542 GM_A67725 - POS | 58.8 |
| pMON83542 GM_A67708 - POS | 39.2 |
| pMON83542 GM_A67737 - POS | 25.1 |
| pMON83542 GM_A67702 - POS | 22.5 |
| pMON83542 GM_A67723 - POS | 19.7 |
| pMON83542 GM_A67730 - POS | 14.8 |

Example 4

Figure 2:
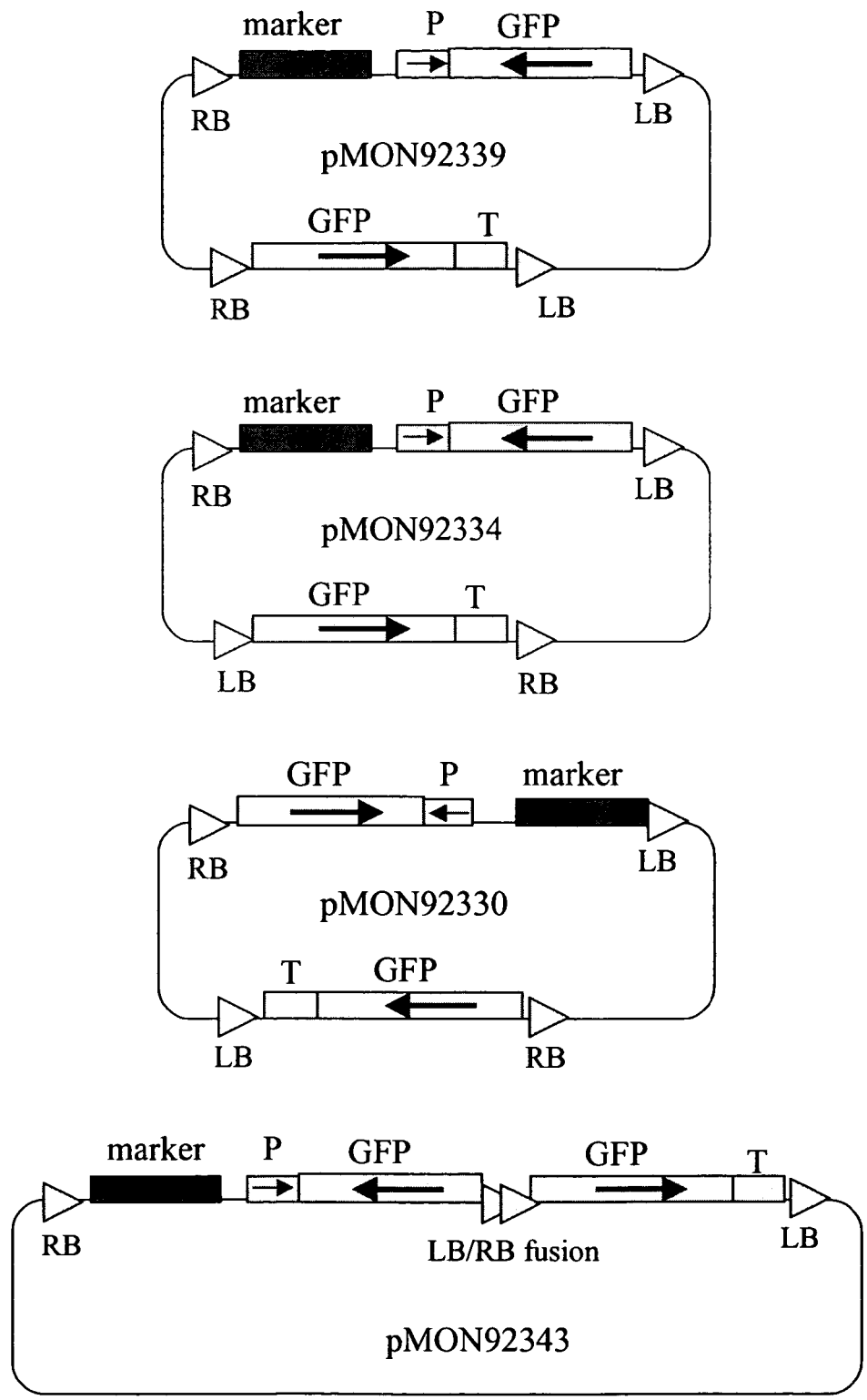
FIGS. 2 and 3 schematically illustrate elements of plasmid vectors.

Three plasmid vectors were prepared to test the in vivo assembly method of gene silencing in transgenic tobacco plants. Plasmid vectors pMON92330, pMON92334 and pMON92339 were identical to each other except for the placement of the right and left T-DNA borders as illustrated in FIG. 2.

All three vectors contain two separate T-DNAs, each flanked by a right and a left border. One of the T-DNAs contains the selectable marker transcription unit (marker) as described in Example 1. In the first T-DNA (T-DNA-1) there is a 300 bp fragment from the 5' end of the green fluorescent protein coding region (GFP) operably linked to an e35S promoter as disclosed in U.S. Pat. No. 5,359,142 (P). The GFP fragment is in the anti-sense orientation relative to the functional orientation of the promoter. The second T-DNA contains the GFP fragment operably linked in a sense orientation to a *Triticum aestivum* heat shock protein 17 (Ta-Hsp 17) polyadenylation DNA (T) as disclosed in U.S. Patent Application Publication US 2002/192813 A1. The vectors have different placements of the right and left T-DNA borders. When vector pMON92330 is used in the methods of this invention, physical linkage of two T-DNA insertions in vivo with a junction across the right borders (RB-RB junction) will result in an intact transcription unit that comprises inverted repeats of the GFP fragments. When vector pMON92334 is used, physical linkage of two T-DNA insertions in vivo with a junction across the left borders (LB-LB junction) will result in an intact transcription unit that comprises inverted repeats of the GFP fragments. And when vector pMON92339 is used, physical linkage of two T-DNA insertions in vivo with a junction across a particular right border and a particular left border (RB-LB junction) will result in an intact transcription unit that comprises inverted repeats of the GFP fragments. As a control, vector pMON92343 was constructed with a single T-DNA flanked by a single right border and a single left border. Between the borders the T-DNA comprised an e35S promoter linked, in series, to an anti-sense GFP fragment, a left border/right border fusion, a sense GFP fragment and a Ta-Hsp17 polyadenylation DNA. The T-DNA provides a transcription unit with an inverted repeat of the GFP fragments. The chimeric left border/right fusion was assembled from T-DNA borders in a way that mimics the predicted assembly that would occur if the two borders were nicked naturally by the VirD protein in Agrobacterium tumefaciens, and then ligated together.

Plasmid vectors pMON92330, pMON92334, pMON92339 and control pMON92341 were transformed into GFP-producing transgenic tobacco plants using Agrobacterium-mediated transformation of leaf discs to generate stable transgenic plants essentially as in Horsch et al., Science 227: 1229-1231 (1985), using glyophosate selection instead of kanamycin. The leaf discs were from plants that were transgenic for the GFP gene expressed under the control of the e35S promoter.

Samples of the R0 plants were collected for analysis by real time PCR (Taqman) (Applied Biosystems, Foster City, Calif.) to quantitate the expression levels of the GFP transgene. Results of measured GFP values are shown in Table 2. When considering the total population of transgenic plants for each vector, the RB-RB configuration (pMON92330) was the most efficient for producing plants in which the GFP gene is suppressed and was essentially as efficient as the control.

TABLE 2

| Vector Description | Percent total Suppression |
|---|---|
| pMON92339 (RB-LB) | 52 |
| pMON92334 (LB-LB) | 51 |
| pMON92330 (RB-RB) | 79 |
| pMON92343 (Control) | 84 |

Southern blots were conducted on transgenic plants made using vectors pMON92330 and pMON92339 to determine the linkage patterns of the T-DNA insertions from the plasmid vectors. Genomic DNA was digested with HindIII and probed sequentially with DNA of the e35S promoter (T-DNA-1) and Ta-Hsp17 polyadenylation DNA (T-DNA-2). Under these conditions, plants in which a band of the same size is obtained with both probes are considered to be linked in a way that creates an intact transcription unit with inverted repeats. As expected, both vectors gave rise to plants with an intact transcription unit, more frequently in the case of vector pMON92330 (RB-RB) than pMON92339 (RB-LB). For both vectors pMON92339 and pMON92330, the plants with a Southern blot result indicating this type of intact transcription unit linkage had lower average GFP expression than the plants that did not (Table 3). This result is consistent with the observation that in vivo assembly of the two T-DNAs can give rise to transgenic plants with linkages that create inverted repeats and that these plants efficiently suppress a target gene. In a certain percentage of events, 2 copies of T-DNA-1 were found to have assembled to form an inverted repeat such that the target gene was suppressed.

TABLE 3

| Construct | Average GFP expression: linked events | Average GFP expression: unlinked events |
|---|---|---|
| pMON92330 (RB-RB) | 0.04 +/− 0.01 | 0.17 +/− 0.06 |
| pMON92339 (RB-LB) | 0.06 +/− 0.03 | 0.24 +/− 0.03 |

Values shown are the average expression values for GFP as measured by Taqman, plus or minus the standard error Example 5

Figure 3:
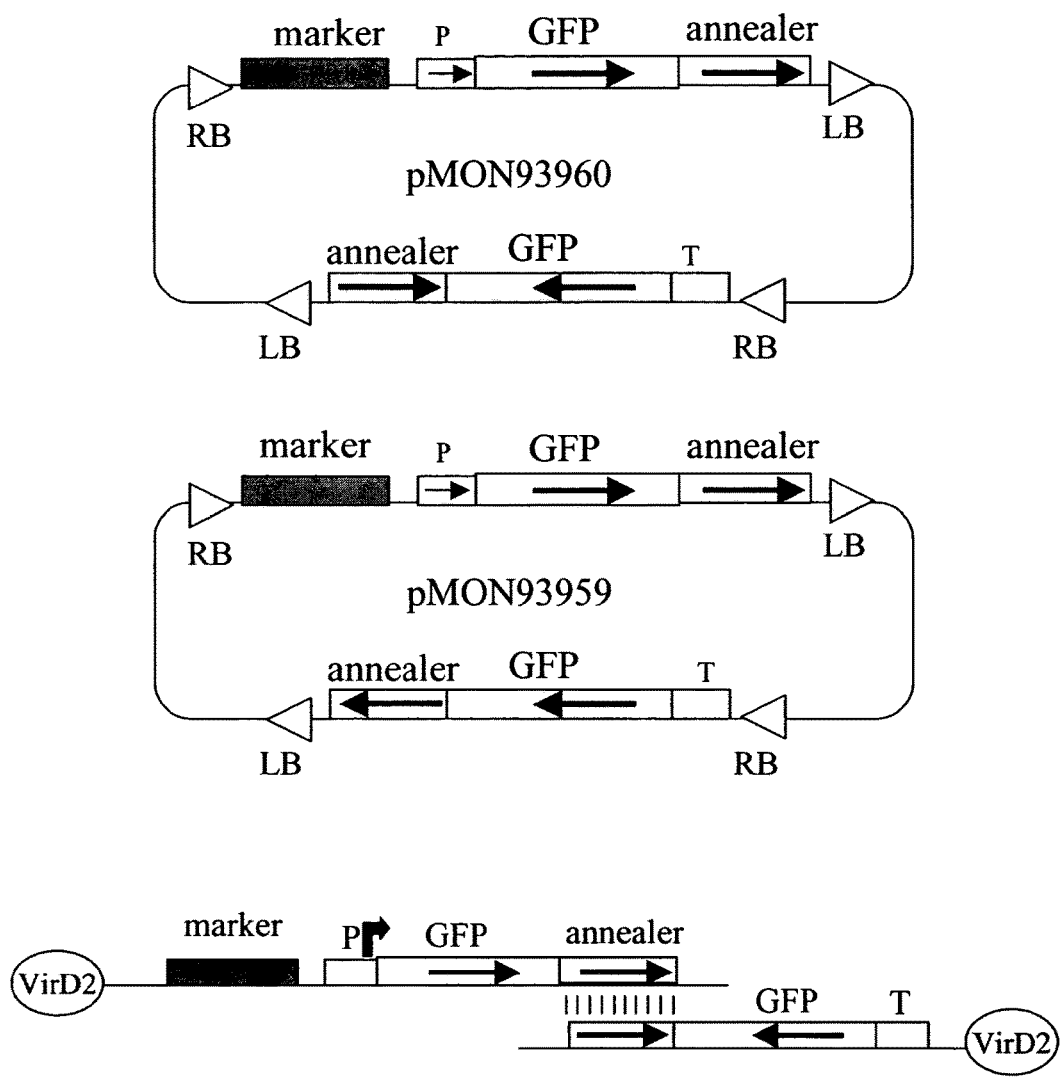

Two plasmid vectors were prepared to test the impact of annealer-assisted in vivo assembly, e.g. between T-strands in an in vivo assembly of a gene suppression transcription unit in transgenic tobacco plants. With reference to FIG. 3 plasmid vectors pMON93959 and pMON93960 were constructed essentially identical to vector pMON92334 (Example 4) but with the addition of common DNA with identical 103 bp on DNA derived from pGEM-Teasy (Promega, Madison, Wis.). The 103 bp piece of DNA is referred to as the "annealer" segment. Both plasmid vectors contained two separate T-DNAs, each flanked by a right and a left border. One of the T-DNAs contained a selectable marker gene essentially as described in Example 1. In the first T-DNA the annealer segment was located between the 3' end of the anti-sense-oriented GFP fragment and the left T-DNA border. In the second T-DNA the annealer fragment was located between the left T-DNA border and the 5' end of the GFP fragment which was operably linked to a Ta-Hsp17 polyadenylation DNA in the sense orientation. Plasmid vectors pMON93959 and pMON93960 were identical to each other except for the orientation of the annealer segment. In pMON93960 the annealer segments are oriented such that there will be 103 bp of complementary DNA near the left borders of the T-strands produced by the two T-DNAs such that they can anneal to each other. In pMON93959, the two segments are oriented such that the T-strands produced from the two T-DNAs do not have substantial complementary DNA and cannot anneal. Thus, pMON93959 is a negative control vector. Annealing of the two T-strands in the region of the annealer segment can result in recombination between the two T-strands which would result in assembly of an intact transcription unit that comprises inverted repeats of the GFP fragments as shown in FIG. 3 without internal T-DNA borders.

Plasmid vectors pMON93959 and pMON93960 were transformed into GFP-producing, transgenic tobacco plants using Agrobacterium-mediated transformation of leaf discs to generate stable transgenic plants. Additional controls were pMON92343 (Example 4) and a vector with just a marker transcription unit.

Samples of the R0 plants were then collected for analysis by real time PCR (Taqman) to quantitate the expression levels of the GFP transgene. The results are shown in Table 4. Plants transformed with plasmid vector pMON93960 had a lower average GFP expression than plants transformed with the negative control plasmid pMON93959, indicating that the presence of a properly oriented annealer segment provides for an embodiment of in vivo assembly.

TABLE 4

| Construct | Average GFP expression | Standard error |
|---|---|---|
| pMON26140 | 486 | +/−46 |
| pMON92343 | 256 | +/−24 |
| pMON93959 | 396 | +/−84 |
| pMON93960 | 138 | +/−26 |

Example 6

This example describes the design of a 3 T-DNA plasmid vector for in vivo assembly of a recombinant transcription unit, which can be used to suppress an endogenous plant gene, and where the third T-DNA containing the selectable marker can be segregated away from the in vivo-assembled recombinant transcription unit. A plasmid vector is prepared with 3 T-DNAs, each flanked by *Agrobacterium* T-DNA border elements, i.e. right border DNA (RB) and left border DNA (LB).

The first T-DNA comprises a left T-DNA border (LB), a promoter (P), transcribable DNA from a gene targeted for suppression (GOI) and right T-DNA border (RB). More specifically, the promoter is a soybean (*G. max*) 7Sa' promoter and the transcribable DNA from a gene targeted for suppression is substantially all of intron 1 of the *G. max* FAD2-1A gene (FAD2 Intron DNA). Although either orientation can be used, in this T-DNA, the FAD2 Intron DNA is in a sense orientation with respect to promoter P.

The second T-DNA contains a left and right T-DNA border between which there is FAD2 Intron DNA in an anti-sense orientation with respect to the RB.

The third T-DNA contains a left and right T-DNA border, between which there is a Marker T/U essentially as described in Example 1.

Following transformation, selection and regeneration, plants are screened by Southern analysis to identify events where the first and second T-DNAs are assembled in vivo to form a transcriptional unit with an inverted repeat of the FAD2 Intron DNA and where the third T-DNA containing the selectable marker is genetically unlinked and can be segregated away in subsequent generations. Transformed plants are self-pollinated producing segregating seed which is screened to identify seeds with the gene suppression transcription unit but without the selectable marker.

Example 7

This example illustrates the design of an engineered *Agrobacterium tumefaciens* strain containing a selectable marker T-DNA on its Ti plasmid and a plasmid vector with 2 T-DNAs for in vivo assembly of a recombinant transcription unit, which can be used to suppress an endogenous plant gene, and where the T-DNA containing the selectable marker can be segregated away from the in vivo-assembled recombinant transcription unit. A plasmid vector is prepared with 2 T-DNAs essentially like the first and second T-DNAs described in Example 6. A third T-DNA with a Marker T/U like the third T-DNA described in Example 6 is located on a Ti plasmid of the *A. tumefaciens* strain.

Following transformation, selection and regeneration, plants are screened by Southern analysis to identify events where the first and second T-DNAs have assembled in vivo to form a gene suppression transcriptional unit and where the third T-DNA containing the selectable marker is genetically unlinked and can be segregated away in subsequent generations. Subsequent generations of the transgenic plant are screened and plants are identified without the selectable Marker T/U and having functional assembled transcription unit for suppressing the FAD2 gene.

All of the materials and methods disclosed and claimed herein can be made and used without undue experimentation as instructed by the above disclosure. Although the materials and methods of this invention have been described in terms of specific embodiments and illustrative examples, it will be apparent to those of skill in the art that variations may be applied to the materials and methods described herein without departing from the concept, spirit and scope of the invention. All such similar substitutes and modifications apparent to those skilled in the art are deemed to be within the spirit, scope and concept of the invention as defined by the appended claims.

What is claimed is:

1. A method of in vivo assembling of a recombinant transcription unit for gene suppression,
said method comprising introducing into a chromosome in the nucleus of a cell a first segment of DNA and a distinct second segment of DNA, each comprising a part of a recombinant transcription unit for gene suppression;
wherein said first segment of DNA comprises a promoter DNA and transcribable DNA from at least one gene targeted for suppression in either a sense or an anti-sense orientation;
wherein said second segment of DNA comprises at least a part of said transcribable DNA;
wherein, when inserted in tandem into a chromosome in a cell, said first and second segments of DNA can form an assembled transcription unit comprising said promoter DNA operably linked to transcribable DNA from the first segment of DNA linked to transcribable DNA from the second segment of DNA and wherein RNA transcribed from said assembled transcription unit is capable of forming double-stranded RNA;
and selecting a transgenic cell in which said double-stranded RNA is produced.

2. The method of claim 1, wherein at least one of said first and second segments of DNA further comprises a selectable marker transcription unit.

3. The method of claim 1, wherein said first and second segments of DNA are introduced from a common plasmid.

4. The method of claim 1, wherein said first and second of said segments of DNA are introduced from separate plasmids.

5. The method of claim 3 further comprising introducing a third segment of DNA comprising a selectable marker transcription unit.

6. The method of claim 5, wherein said third segment of DNA is introduced from a second plasmid.

7. The method of claim 1, wherein said first segment of DNA comprises a promoter DNA and DNA from at least one gene targeted for suppression in an anti-sense orientation with respect to transcription initiated by said promoter.

8. The method of claim 3, wherein said first and second segments of DNA are T-DNAs which are co-integrated into the genome of an eukaryotic organism by *Agrobacterium tumefaciens*-mediated transformation using a plasmid vector comprising said T-DNAs, wherein said plasmid vector comprises
(a) a first T-DNA comprising, between left and right T-DNA borders, a promoter which is operable in said eukaryotic organism operably linked to DNA from at least one gene targeted for suppression;
(b) a second T-DNA comprising, between left and right T-DNA borders, at least part of said DNA from at least one gene targeted for suppression.

9. The method of claim 8, wherein said DNA from one or more genes targeted for suppression in said first T-DNA is adjacent to a right T-DNA border and wherein said at least part of said DNA from one or more genes targeted for suppression in said second T-DNA is located adjacent to a right T-DNA border.

10. The method of claim 8, wherein said organism is a plant.

11. The method of claim 8, wherein in each of said T-DNAs there is common DNA of identical sequence adjacent to one of said T-DNA borders, wherein said common DNA is oriented in each T-DNA to enable annealing of T-strands produced from the two T-DNAs, whereby said borders are eliminated from the assembled transcription unit.

12. The method of claim 8, wherein DNA from at least one gene targeted for suppression in said first T-DNA is in an anti-sense orientation with respect to transcription initiated by said promoter.

13. A plasmid vector for *Agrobacterium tumefaciens*-mediated, tandem co-integration of two T-DNAs into the genome of a plant for in vivo assembly of a gene suppression transcription unit, wherein said plasmid vector comprises
   (a) a first T-DNA comprising in series a promoter which is operable in said plant, DNA from at least one gene targeted for suppression and a T-DNA border; and
   (b) a second T-DNA comprising in series a T-DNA border and at least a part of said DNA from at least one gene targeted for suppression;
wherein, when said first and second T-DNAs are co-integrated in tandem and joined at said T-DNA borders, a transcription unit is formed comprising said promoter operably linked to DNA from at least one gene targeted for suppression; and wherein RNA transcribed by said transcription unit can form double-stranded RNA.

14. The plasmid vector of claim 13, wherein at least one of said T-DNAs further comprises a marker gene transcription unit.

15. The plasmid vector of claim 13, wherein said T-DNAs are co-integrated in tandem and joined at T-DNA borders which are
   (a) both right T-DNA borders,
   (b) both left T-DNA borders, or
   (c) one left T-DNA border and one right T-DNA border.

16. The plasmid vector of claim 13, wherein in each of said T-DNAs there is common DNA of identical sequence adjacent to one of said T-DNA borders, wherein said common DNA is oriented in each T-DNA to enable annealing of T-strands produced from the two T-DNAs, whereby said borders are eliminated from the assembled transcription unit.

17. The plasmid vector of claim 13 in which DNA from at least one gene targeted for suppression in said first T-DNA is in an anti-sense orientation with respect to DNA transcribed by said promoter.

18. A method of in vivo assembling of a recombinant transcription unit for gene suppression from two T-DNAs which are co-integrated in tandem into the genome of an eukaryotic organism by *Agrobacterium tumefaciens*-mediated transformation using a binary plasmid vector comprising said T-DNAs, said method comprising introducing into a cell of said organism a said binary plasmid vector comprising said two T-DNAs and a tumor-inducing plasmid;
   wherein said first T-DNA comprises, in series, a promoter, transcribable DNA from at least one gene targeted for suppression in an anti-sense orientation and a T-DNA border and said second T-DNA comprises, in series, a T-DNA border and at least a part of said transcribable DNA in a sense orientation with respect to said border;
   wherein, when inserted in tandem into a chromosome in said organism, said first and second T-DNAs can form an assembled transcription unit comprising said promoter operably linked to transcribable DNA from the first T-DNA linked to T-DNA border linked to transcribable DNA from the second T-DNA; and wherein RNA transcribed from said assembled transcription unit is capable of forming double-stranded RNA; and selecting a transgenic cell in which said double-stranded RNA is produced.

19. The method of claim 18, wherein said organism is a plant.

20. The method of claim 18, wherein at least one of the T-DNAs comprises a selectable marker transcription unit.

* * * * *